US008469890B2

(12) United States Patent
Langeland et al.

(10) Patent No.: US 8,469,890 B2
(45) Date of Patent: *Jun. 25, 2013

(54) SYSTEM AND METHOD FOR COMPENSATING FOR MOTION WHEN DISPLAYING ULTRASOUND MOTION TRACKING INFORMATION

(75) Inventors: Stian Langeland, Vestfold (NO); Andreas Heimdal, Oslo (NO)

(73) Assignee: General Electric Company, Schenectady, NY (US)

( * ) Notice: Subject to any disclaimer, the term of this patent is extended or adjusted under 35 U.S.C. 154(b) by 899 days.

This patent is subject to a terminal disclaimer.

(21) Appl. No.: 12/410,427

(22) Filed: Mar. 24, 2009

(65) Prior Publication Data

US 2010/0249592 A1   Sep. 30, 2010

(51) Int. Cl.
*A61B 8/00* (2006.01)
(52) U.S. Cl.
USPC ............ 600/438; 382/107; 600/437; 600/450
(58) Field of Classification Search
USPC ..................... 600/437, 438, 450; 382/107
See application file for complete search history.

(56) References Cited

U.S. PATENT DOCUMENTS

| 6,201,900 | B1* | 3/2001 | Hossack et al. | 382/294 |
|---|---|---|---|---|
| 6,464,643 | B1* | 10/2002 | Brock-Fisher | 600/458 |
| 2003/0036703 | A1* | 2/2003 | Li | 600/437 |
| 2003/0105401 | A1* | 6/2003 | Jago et al. | 600/443 |
| 2004/0208341 | A1* | 10/2004 | Zhou et al. | 382/103 |
| 2005/0074154 | A1* | 4/2005 | Georgescu et al. | 382/128 |
| 2006/0058673 | A1* | 3/2006 | Aase et al. | 600/450 |
| 2007/0014445 | A1* | 1/2007 | Lin | 382/128 |
| 2007/0167809 | A1* | 7/2007 | Dala-Krishna | 600/459 |
| 2008/0095417 | A1* | 4/2008 | Pedrizzetti et al. | 382/128 |
| 2009/0028404 | A1* | 1/2009 | Bussadori et al. | 382/130 |

* cited by examiner

*Primary Examiner* — Long V. Le
*Assistant Examiner* — Ellsworth Weatherby
(74) *Attorney, Agent, or Firm* — The Small Patent Law Group; Dean D. Small

(57) ABSTRACT

A system and method for compensating for motion with displaying ultrasound motion tracking information are provided. The method includes obtaining ultrasound image data of an imaged object and determining motion tracking information based on the ultrasound image data. The method further includes compensating for motion of the imaged object based on the determined motion tracking information and generating motion compensated ultrasound image data in combination with motion tracking indicators based on the motion compensation.

23 Claims, 8 Drawing Sheets

SYSTEM AND METHOD FOR COMPENSATING FOR MOTION WHEN DISPLAYING ULTRASOUND MOTION TRACKING INFORMATION

BACKGROUND OF THE INVENTION

The subject matter disclosed herein relates generally to diagnostic imaging systems, and more particularly, to ultrasound imaging systems providing motion tracking, especially for cardiac imaging.

Medical imaging systems are used in different applications to image different regions or areas (e.g., different organs) of patients. For example, ultrasound imaging systems are finding use in an increasing number of applications, such as to generate images of the heart. In heart imaging applications, motion tracking of the muscles of the heart based on acquired ultrasound images of the heart also may be provided using, for example, two-dimensional (2D) or three-dimensional (3D) speckle tracking. Speckle tracking uses speckle information in the acquired images to track motion, such as motion of the myocardium of the imaged heart. These images are then displayed for review and analysis by a user, which may include 2D strain analysis of myocardial deformation.

In order to ensure that the tracking was performed properly, a user typically reviews a display showing tracking information, which may include a graphical overlay. For example, some known ultrasound systems that provide motion tracking information use curved anatomical M-mode grayscale imaging from a tracked centerline of the imaged heart. When performing cardiac image motion tracking in these known systems, the user thereafter compares the relative motion of the imaged heart and an overlay representing the tracked motion to determine whether the tracking was performed properly. However, because the error in tracking is typically much smaller than the muscle motion of the heart, it is often difficult to determine whether the tracking is correct, and if incorrect, where exactly the motion tracking failed. Additionally, the muscle motion is also fast, thereby making it difficult to follow the overlay (e.g., moving dots), especially in the early relaxation stage of the heart. Accordingly, using known ultrasound systems displaying tracking information, it is often very difficult to visually confirm motion tracking results, for example, because the markings provided as part of the overlay move too quickly or correlate too much with the motion of the heart. Thus, users may improperly confirm tracked motion.

BRIEF DESCRIPTION OF THE INVENTION

In accordance with an embodiment of the invention, a method for compensating for motion in an imaged ultrasound object is provided. The method includes obtaining ultrasound image data of an imaged object and determining motion tracking information based on the ultrasound image data. The method further includes compensating for motion of the imaged object based on the determined motion tracking information and generating motion compensated ultrasound image data in combination with motion tracking indicators based on the motion compensation.

In accordance with another embodiment of the invention, a computer readable medium having computer readable code readable by a machine and with instructions executable by the machine to perform a method of compensating for motion in ultrasound imaging is provided. The method includes determining motion tracking information of a region of interest of an imaged object and using the motion tracking information to reduce motion of the imaged object. The method further includes generating motion compensated ultrasound image data in combination with motion tracking indicators having the reduced motion.

In accordance with yet another embodiment of the invention, an ultrasound imaging system is provided that includes an ultrasound probe configured to acquire images of an object. The ultrasound imaging system further includes a processor having a motion compensation module configured to compensate for motion of the imaged object based on determined motion tracking information and generate motion compensated ultrasound image data in combination with motion tracking indicators based on the motion compensation.

DETAILED DESCRIPTION OF THE INVENTION

Figure 1:
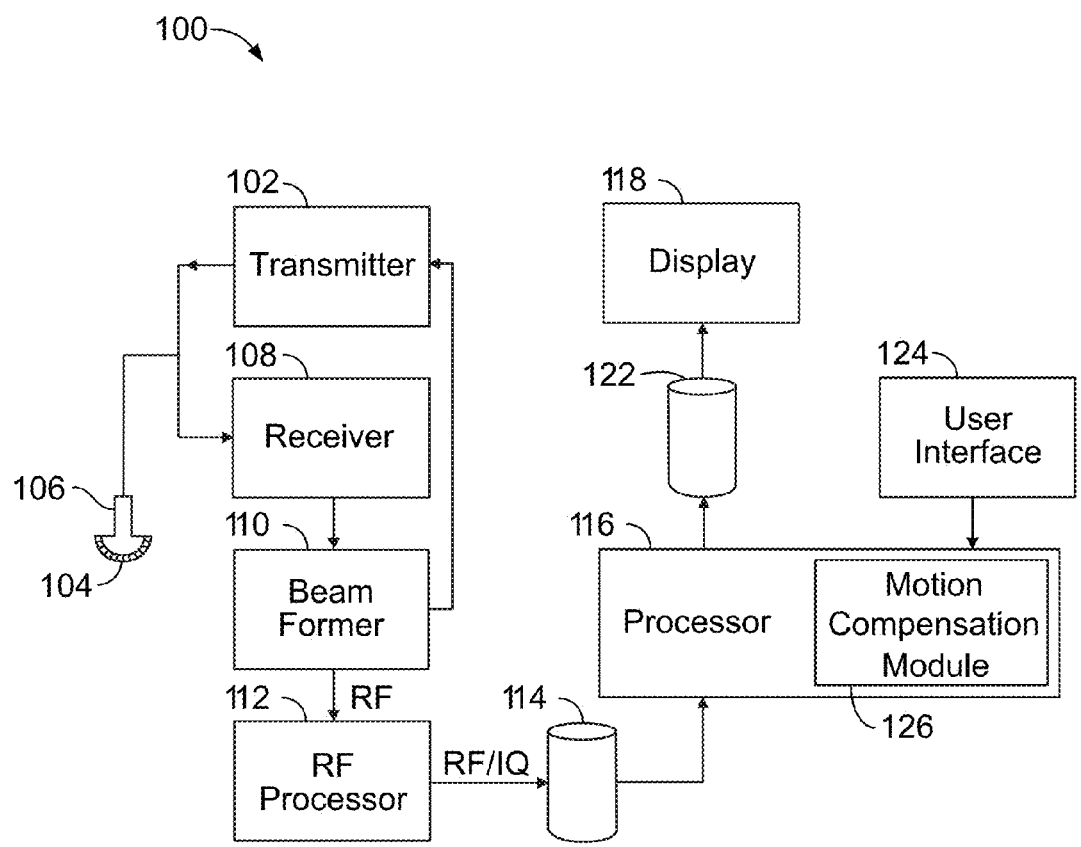
FIG. 1 is a block diagram of a diagnostic ultrasound imaging system configured to compensate for motion in a displayed ultrasound image in accordance with various embodiments of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of ultrasound imaging systems and methods for tracking motion and displaying tracked motion information in combination with a motion compensated image are described in detail below. In particular, a detailed description of an exemplary ultrasound imaging system will first be provided followed by a detailed description of various embodiments of methods and systems for generating and displaying ultrasound motion tracking information, especially cardiac motion tracking information in combination with a motion compensated image.

At least one technical effect of the various embodiments of the systems and methods described herein include removing motion from a displayed image to allow easier distinction of good motion tracking quality from poor motion tracking quality based on displayed tracking indicators. The various embodiments allow quicker and more robust identification of regions of a tracked object (e.g., based on speckle tracking) where motion tracking has failed. Moreover, a user is able to provide an input indicating where and how the tracking failed.

FIG. 1 is a block diagram of an ultrasound system 100 constructed in accordance with various embodiments of the invention. The ultrasound system 100 is capable of steering (mechanically and/or electronically) a soundbeam in 3D space, and is configurable to acquire information corresponding to a plurality of two-dimensional (2D) or three-dimensional (3D) representations or images of a region of interest (ROI) in a subject or patient. One such ROI may be a human heart or the myocardium (muscles) of a human heart. The ultrasound system 100 is also configurable to acquire 2D and 3D images in one or more planes of orientation. In operation, real-time ultrasound imaging using a 2D or 3D ultrasound probe may be provided.

The ultrasound system 100 includes a transmitter 102 that, under the guidance of a beamformer 110, drives an array of elements 104 (e.g., piezoelectric elements) within a probe 106 to emit pulsed ultrasonic signals into a body. A variety of geometries may be used. The ultrasonic signals are back-scattered from structures in the body, like blood cells or muscular tissue, to produce echoes that return to the elements 104. The echoes are received by a receiver 108. The received echoes are passed through the beamformer 110, which performs receive beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to a memory 114 for storage.

In the above-described embodiment, the beamformer 110 operates as a transmit and receive beamformer. In an alternative embodiment, the probe 106 includes a 2D array with sub-aperture receive beamforming inside the probe. The beamformer 110 may delay, apodize and sum each electrical signal with other electrical signals received from the probe 106. The summed signals represent echoes from the ultrasound beams or lines. The summed signals are output from the beamformer 110 to an RF processor 112. The RF processor 112 may generate different data types, such as B-mode, color Doppler (velocity/power/variance), tissue Doppler (velocity), and Doppler energy, for one or more scan planes or different scanning patterns. For example, the RF processor 112 may generate tissue Doppler data for multiple (e.g., three) scan planes. The RF processor 112 gathers the information (e.g. I/Q, B-mode, color Doppler, tissue Doppler, and Doppler energy information) related to multiple data slices and stores the data information with time stamp and orientation/rotation information in an image buffer 114.

Orientation/rotation information may indicate the angular rotation of one data slice with respect to a reference plane or another data slice. For example, in a tri-plane implementation wherein ultrasound information is acquired substantially simultaneously or consecutively within a short period of time (e.g. 1/20 second) for three differently oriented scan planes or views, one data slice may be associated with an angle of 0 degrees, another with an angle of 60 degrees, and a third with an angle of 120 degrees. Thus, data slices may be added to the image buffer 114 in a repeating order of 0 degrees, 60 degrees, 120 degrees, . . . , 0 degrees, 60 degrees, and 120 degrees, . . . . Alternatively, instead of storing orientation/rotation information, a data slice sequence number may be stored with the data slice in the image buffer 114. Thus, data slices may be ordered in the image buffer 114 by repeating sequence numbers, e.g. 1, 2, 3, . . . , 1, 2, 3, . . . . The data slices stored in the image buffer 114 are processed by 2D display processors as described in more detail herein.

The ultrasound system 100 also includes a processor 116 to process the acquired ultrasound information (e.g., RF signal data or IQ data pairs) and prepare frames of ultrasound information, which may include motion tracking information, for display on a display 118. The processor 116 is adapted to perform one or more processing operations according to a plurality of selectable ultrasound modalities on the acquired ultrasound data. Acquired ultrasound data may be processed and displayed in real-time during a scanning session as the echo signals are received. Additionally or alternatively, the ultrasound data may be stored temporarily in memory 114 during a scanning session and then processed and displayed in an off-line operation.

The processor 116 is connected to a user interface 124 that may control operation of the processor 116 and receive user inputs as explained below in more detail. The user interface 124 may include hardware components (e.g., keyboard, mouse, trackball, etc.), software components (e.g., a user display) or a combination thereof. The processor 116 also includes a motion compensation module 126 that performs motion compensation to remove motion, particularly overall or gross motion, from a displayed imaged that includes motion tracking indicators.

The display 118 includes one or more monitors that present patient information, including diagnostic ultrasound images to the user for diagnosis and analysis (e.g., images with motion tracking information). One or both of memory 114 and memory 122 may store 3D data sets of the ultrasound data, where such 3D data sets are accessed to present 2D (and/or 3D images) as described herein. The images may be modified and the display settings of the display 118 also manually adjusted using the user interface 124.

It should be noted that although the various embodiments may be described in connection with an ultrasound system, the methods and systems described herein are not limited to ultrasound imaging or a particular configuration thereof. In particular, the various embodiments may be implemented in connection with different types of imaging, including, for example, magnetic resonance imaging (MRI) and computed-tomography (CT) imaging or combined imaging systems. Further, the various embodiments may be implemented in other non-medical imaging systems, for example, non-destructive testing systems.

Figure 2:
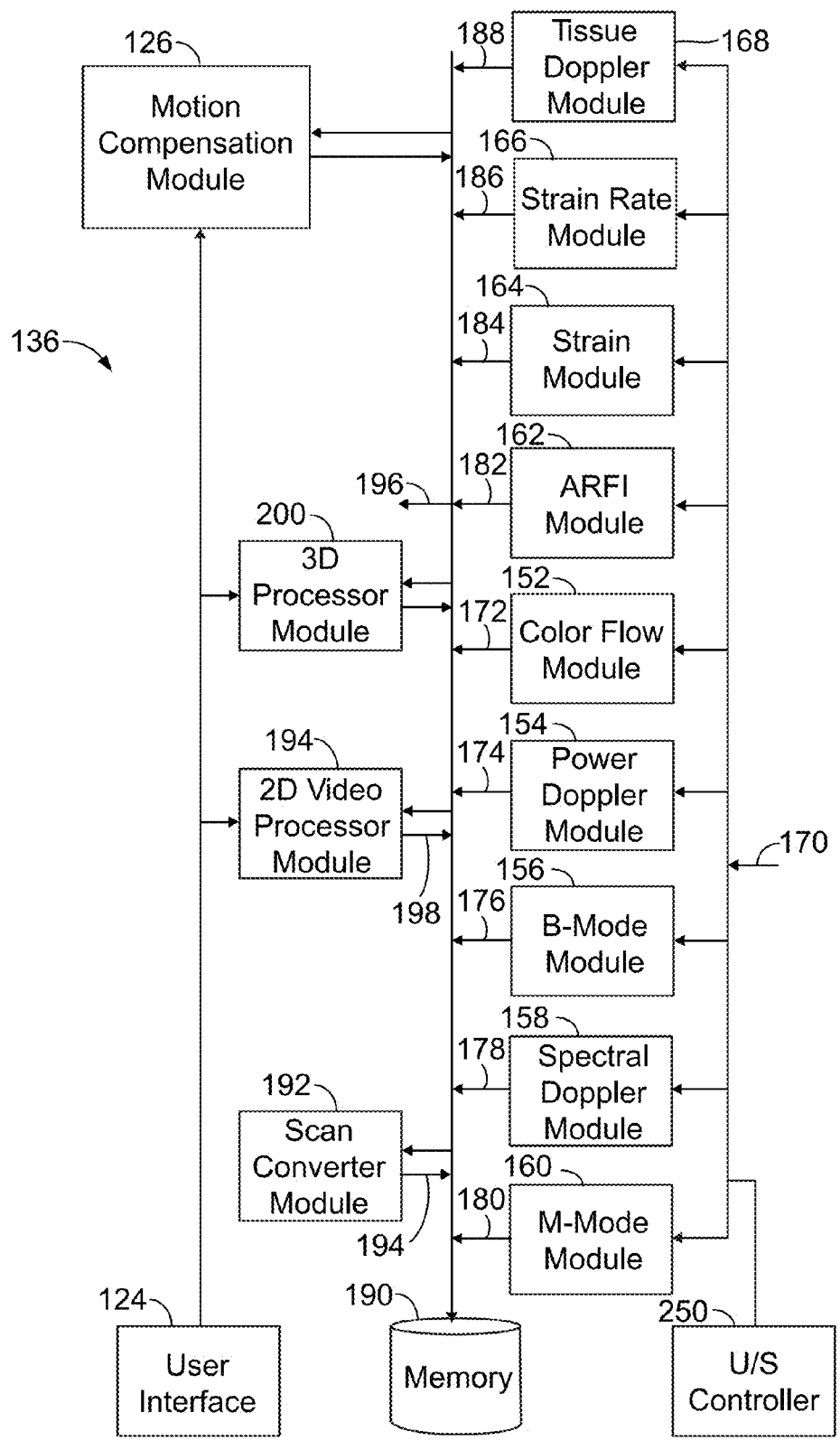
FIG. 2 is a block diagram of an ultrasound processor module of the diagnostic ultrasound imaging system of FIG. 1 formed in accordance with various embodiments of the invention.

FIG. 2 illustrates an exemplary block diagram of an ultrasound processor module 136, which may be embodied as the processor 116 of FIG. 1 or a portion thereof. The ultrasound processor module 136 is illustrated conceptually as a collection of sub-modules, but may be implemented utilizing any combination of dedicated hardware boards, DSPs, processors, etc. Alternatively, the sub-modules of FIG. 2 may be implemented utilizing an off-the-shelf PC with a single processor or multiple processors, with the functional operations distributed between the processors. As a further option, the sub-modules of FIG. 2 may be implemented utilizing a hybrid configuration in which certain modular functions are performed utilizing dedicated hardware, while the remaining modular functions are performed utilizing an off-the shelf PC and the like. The sub-modules also may be implemented as software modules within a processing unit.

The operations of the sub-modules illustrated in FIG. 2 may be controlled by a local ultrasound controller 150 or by the processor module 136. The sub-modules 152-168 perform mid-processor operations. The ultrasound processor module 136 may receive ultrasound data 170 in one of several forms. In the embodiment of FIG. 2, the received ultrasound data 170 constitutes I,Q data pairs representing the real and imaginary components associated with each data sample. The I,Q data pairs are provided to one or more of a color-flow sub-module 152, a power Doppler sub-module 154, a B-mode sub-module 156, a spectral Doppler sub-module 158 and an M-mode sub-module 160. Optionally, other sub-modules may be included such as an Acoustic Radiation Force Impulse (ARFI) sub-module 162, a strain module 164, a strain rate sub-module 166, a Tissue Doppler (TDE) sub-module 168, among others. The strain sub-module 162, strain rate sub-module 166 and TDE sub-module 168 together may define an echocardiographic processing portion.

Each of sub-modules 152-168 are configured to process the I,Q data pairs in a corresponding manner to generate color-flow data 172, power Doppler data 174, B-mode data 176, spectral Doppler data 178, M-mode data 180, ARFI data 182, echocardiographic strain data 182, echocardiographic strain rate data 186 and tissue Doppler data 188, all of which may be stored in a memory 190 (or memory 114 or memory 122 shown in FIG. 1) temporarily before subsequent processing. The data 172-188 may be stored, for example, as sets of vector data values, where each set defines an individual ultrasound image frame. The vector data values are generally organized based on the polar coordinate system.

A scan converter sub-module 192 access and obtains from the memory 190 the vector data values associated with an image frame and converts the set of vector data values to Cartesian coordinates to generate an ultrasound image frame 194 formatted for display. The ultrasound image frames 194 generated by the scan converter module 192 may be provided back to the memory 190 for subsequent processing or may be provided to the memory 114 or the memory 122.

Once the scan converter sub-module 192 generates the ultrasound image frames 194 associated with, for example, the strain data, strain rate data, and the like, the image frames may be restored in the memory 190 or communicated over a bus 196 to a database (not shown), the memory 114, the memory 122 and/or to other processors, for example, the motion compensation module 126.

As an example, it may be desirable to view functional ultrasound images or associated data (e.g., strain curves or traces) relating to echocardiographic functions in real-time on the display 118 (shown in FIG. 1) or view in a post-processing operation tracking information displayed in combination with an image of a motion tracked object. To do so, the scan converter sub-module 192 obtains strain or strain rate vector data sets for images stored in the memory 190. The vector data is interpolated where necessary and converted into an X,Y format for video display to produce ultrasound image frames. The scan converted ultrasound image frames are provided to a display controller (not shown) that may include a video processor that maps the video to a grayscale mapping for video display (e.g., 2D gray-scale projection). The grayscale map may represent a transfer function of the raw image data to displayed gray levels. Once the video data is mapped to the grayscale values, the display controller controls the display 118 (shown in FIG. 1), which may include one or more monitors or windows of the display, to display the image frame. The echocardiographic image displayed in the display 118 is produced from image frames of data in which each datum indicates the intensity or brightness of a respective pixel in the display. In this example, the displayed image represents muscle motion in a region of interest being imaged based on 2D tracking applied to, for example, a multi-plane image acquisition.

Referring again to FIG. 2, a 2D video processor sub-module 194 combines one or more of the frames generated from the different types of ultrasound information. For example, the 2D video processor sub-module 194 may combine a different image frames by mapping one type of data to a gray-scale map and mapping the other type of data to a color map for video display. In the final displayed image, color pixel data may be superimposed on the grayscale pixel data to form a single multi-mode image frame 198 (e.g., functional image) that is again re-stored in the memory 190 or communicated over the bus 196. Successive frames of images may be stored as a cine loop in the memory 190 or memory 122 (shown in FIG. 1). The cine loop represents a first in, first out circular image buffer to capture image data that is displayed in real-time to the user. The user may freeze the cine loop by entering a freeze command at the user interface 124. The user interface 124 may include, for example, a keyboard and mouse and all other input controls associated with inputting information into the ultrasound system 100 (shown in FIG. 1).

A 3D processor sub-module 200 is also controlled by the user interface 124 and accesses the memory 190 to obtain 3D ultrasound image data and to generate three dimensional images, such as through volume rendering or surface rendering algorithms as are known. The three dimensional images may be generated utilizing various imaging techniques, such as ray-casting, maximum intensity pixel projection and the like.

The motion compensation module 126 is also controlled by the user interface 124 and accesses the memory 190 to obtain ultrasound information, and as described in more detail below, generates motion tracking information (with motion tracking indicators) for display, wherein motion of a displayed object (e.g., imaged heart) displayed in combination with the motion tracking information is reduced or eliminated.

More particularly, a method 210 for compensating for motion in an image, particularly an ultrasound image, having motion tracking information displayed in combination therewith is provided. It should be noted that although the method 210 is described in connection with ultrasound imaging having particular characteristics, the various embodiments are not limited to ultrasound imaging or to any particular imaging characteristics. For example, although the method is described in connection with speckle tracking, any type of motion tracking may be implemented. As another example, although the method is described in connection with a particular method for reducing or removing motion from an image, other methods to reduce or remove motion may be implemented.

Figure 4:
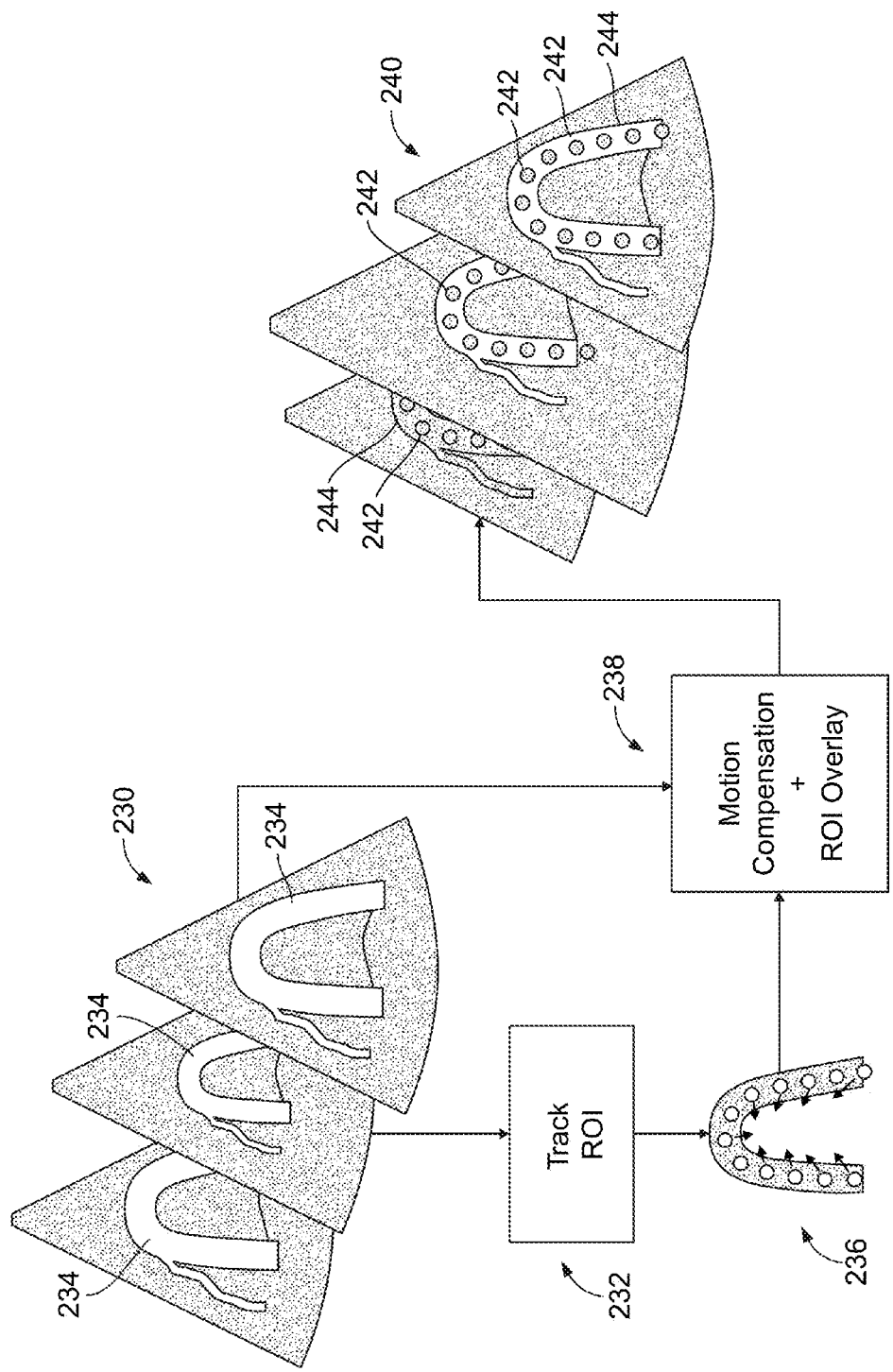
FIG. 4 is a diagram illustrating motion compensation in accordance with various embodiments of the invention.

The method 210 includes obtaining ultrasound data of an imaged object at 212. For example, the ultrasound data may include a plurality of frames of 2D images of a moving heart, which may be combined to form a 3D image of a moving heart at one or more different points in the heart cycle. For example, as shown in FIG. 4, a temporal image sequence 230 of an imaged heart may be acquired. As used herein, obtaining ultrasound data can refer to a scanning operation to acquire the ultrasound data or accessing stored ultrasound data previously acquired. Additionally, the 3D images may be combined to form a four-dimensional (4D) image data set representing an imaged heart over a certain time period, for example, over one or more heart cycles. The 4D image data may be displayed in different forms, such as in a cine loop. It should be noted that the frames of ultrasound data may be combined in any suitable manner known in the art.

Motion tracking of a region of interest (ROI) of the object based on the ultrasound data is then performed at 214. For example, in a cardiac application, the ROI may be the myocardium of the heart. In some embodiments, the motion tracking is performed in a post-processing operation, but is not limited to only being performed in a post-processing operation. The motion tracking may be performed in different ways, for example, using speckle tracking. Speckle tracking uses noise correlated to the motion of an ultrasound probe to identify motion of an imaged object. Speckle generally results from the coherent reflection of small cells contained in soft tissues. In the various embodiments, motion information relating to an imaged object may be acquired, for example, using automatic tracking methods known in the art for tracking motion of tissue (e.g., myocardium) in 2D or 3D. For example, 3D speckle tracking may be used to track motion. One example of motion tracking for cardiac applications that may be used is described in U.S. Pat. No. 6,994,673 entitled "Method and Apparatus for Quantitative Myocardial Assessment" and that is commonly owned.

The motion tracking information may be stored and correspond to motion of an imaged object, such as an imaged heart over time. The motion tracking information may correspond to motion tracking in 2D or 3D. For example, in a cardiac application, the motion tracking information may correspond to a plurality of images of an imaged heart over one or more heart cycles.

Accordingly, as shown in FIG. 4 a tracked ROI 232 is determined from motion tracking of the temporal image sequence 230. In the illustrated example, the tracked ROI 232 corresponds to a myocardium 234 of an imaged heart in the temporal image sequence 230.

Figure 3:
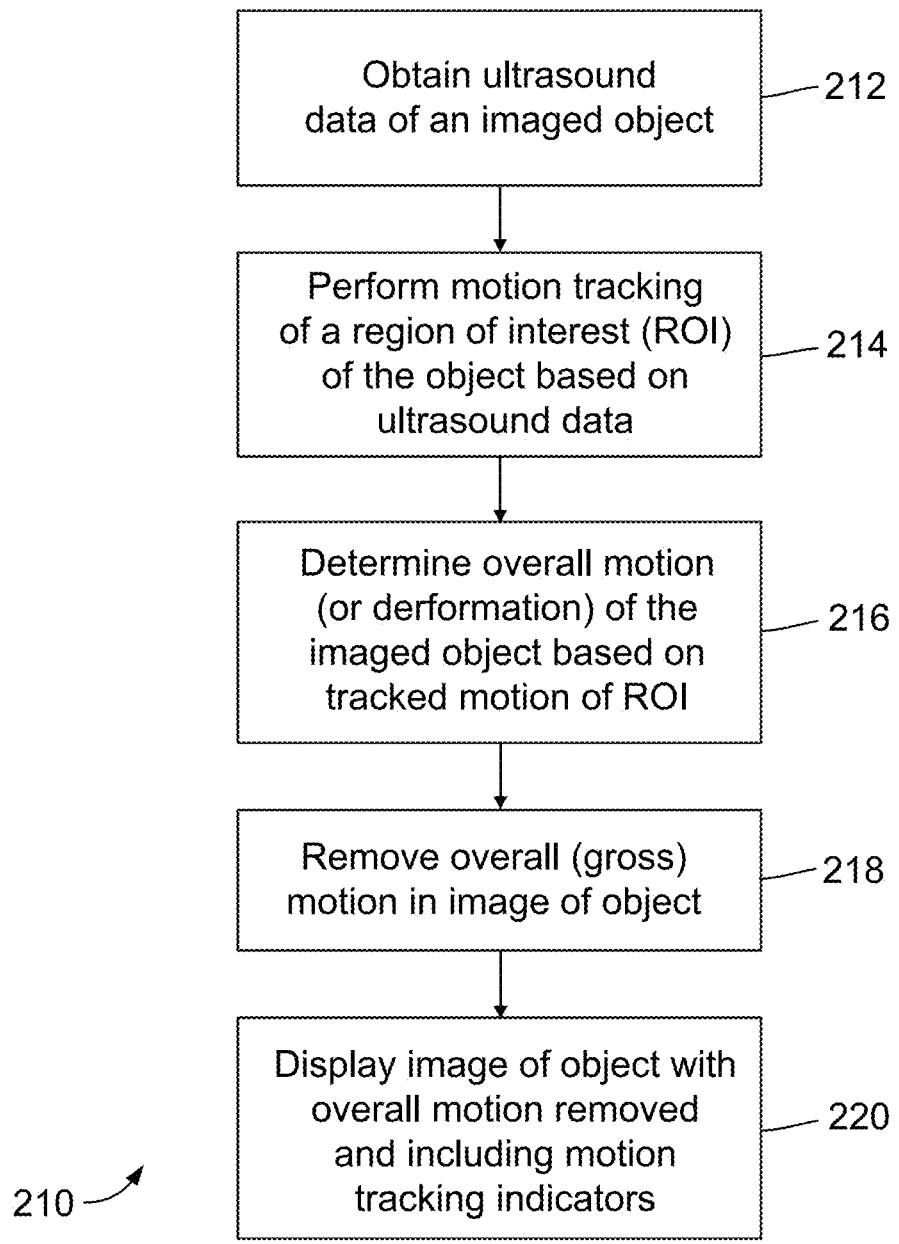
FIG. 3 is a flowchart of method for compensating for motion in an ultrasound image having motion tracking information displayed in combination therewith in accordance with various embodiments of the invention.

Referring again to the method 210 of FIG. 3, using the motion tracking information acquired from the motion tracking of the ROI, an overall motion (or deformation) of the imaged object based on the tracked motion of the ROI is determined at 216. For example, using the motion of the myocardium, the overall motion of the heart is determined. The determination of motion may be based on a displacement field 236 (as shown in FIG. 4) corresponding to tracked motion at different points along a surface of the imaged object, for example, at different points along the myocardium of the heart. In various embodiments, the various points in the displacement field 236 correspond to a deformation or shape change of the ROI, namely the myocardium of the heart. Using this displacement information, the amount of movement, and accordingly, the amount of deformation or shape change at each of the points along the ROI can be determined, which can be used to determine an overall deformation or shape change of the entire ROI. The deformation or shape change of the ROI is also representative of the movement, and corresponding deformation or shape change of the object having the ROI. Thus, by determining the deformation or shape change of the ROI, the overall deformation or shape change of the object may be determined.

After the overall motion or deformation of the object is determined, the overall motion or deformation is removed or reduced from (e.g., compensated for) the image of the object at 218. For example, in a cardiac application, overall or gross motion of an imaged heart is reduced or removed such that the displayed image of the heart, which may be used to confirm motion tracking quality, has reduced or minimized motion. Using the overall motion or deformation information (of the ROI) compensation of the overall motion or deformation is performed. In various embodiments, the compensation for the determined motion or deformation includes subtracting the overall motion or deformation from the image dataset, thereby effectively removing an average motion from the image. In some embodiments, the motion or deformation compensation includes at least one of scaling, rotating and/or translating the image based on the overall motion or deformation. For example, using the overall motion or deformation, an affine transformation of the image is performed. The affine transformation may include transformation between two vector spaces that includes a linear transformation followed by a translation.

In general, an affine transformation performed in accordance with various embodiments includes one or more linear transformations (e.g., rotation, scaling or shear) and a translation (or shift). It should be noted that more than one linear transformation may be combined into a single transformation. It also should be noted that a non-affine transformation of the image based on the overall motion or deformation may be performed.

The scaling, rotating and/or translating compensation results in overall (or gross motion) being reduced in or eliminated from the image of the object. Thus, as shown in FIG. 4, a motion compensation process 238 is performed to reduce or remove overall or gross motion from the temporal image sequence 230 by removing overall or gross motion of the heart from the image frames of the imaged heart. An ROI overlay may also be added to identify the ROI and includes motion tracking indicators that may be used to assess the quality of the tracked motion.

It should be noted that motion compensation according to the method 210 can be applied to an entire image or to a portion or smaller part of the image. For example, in a cardiac application, the method 210 can be applied to an image of the entire heart or to a single cardiac segment or wall.

One or more images of the object with overall motion or deformation removed then may be displayed at 220. For example, as shown in FIG. 4, a motion compensated image sequence 240 may be displayed, which has reduced or removed image motion. A plurality of motion tracking indicators 242 also may be displayed as part of an ROI overlay 244. For example, in a cardiac application, the ROI overlay 244 may generally encompass the myocardium of the heart and includes color coding indicating different regions of the myocardium. It should be noted that although the motion tracking indicators 242 are illustrated as dots, different sized and shaped indicators may be provided. In general, the motion tracking indicators 242 can be any displayed indicators that allow a user to assess motion tracking, and in particular, a quality of motion tracking at different portions of the imaged object, illustrated as a heart. For example, the motion tracking indicators 242 are generally configured to allow a user to determine the amount and direction of movement of the motion tracking indicators 242 relative to the imaged object. The ROI overlay 244 with motion tracking indicators 242 are generated using any known method to indicate tracked motion. For example, the tracking indicators 242 may be generated based on a velocity gradient or velocity vector at each of the points defined by the tracking indicators 242 and calculated from the tracked motion as described in more detail herein.

Figure 5:
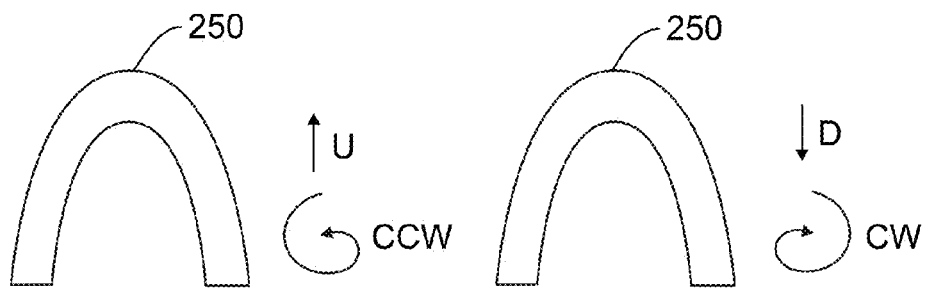
FIG. 5 is a diagram illustrating motion compensation of a myocardium of a heart in accordance with various embodiments of the invention.

Thus, various embodiments compensate for overall or gross motion in an image by reducing or removing the overall or gross motion, thereby facilitating visual qualification of the tracking of an ROI. For example, in a cardiac application, and as shown in FIG. 5, tracked motion of an ROI (illustrated as the myocardium of the heart), is used to compensate for the overall motion of the imaged heart. As shown, the imaged heart is exhibiting gross or overall motion in upward and counterclockwise directions represented by the arrow U and the arrow CCW, respectively. In order to compensate for the gross motion, based on motion tracking, the various embodiments remove the tracked motion by applying motion compensation in downward and clockwise directions represented by the arrow D and the arrow CW, respectively. The amount and direction of motion subtracted from the images are based on the direction and amount of tracked motion.

Figure 6:
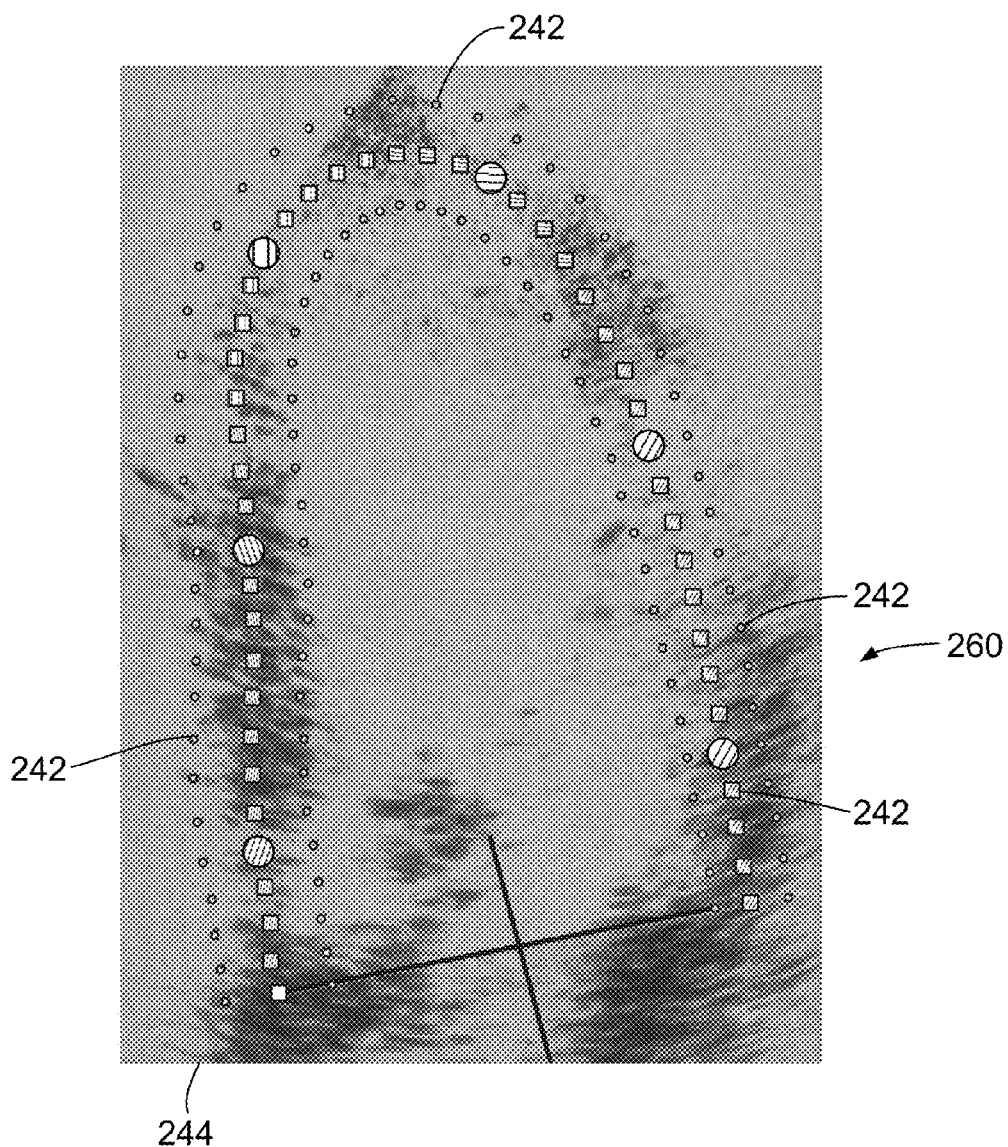
FIG. 6 is a motion compensated ultrasound image of an imaged heart having motion tracking indicators displayed in connection therewith in accordance with various embodiments of the invention.

Accordingly, the various embodiments use tracked or determined motion and/or deformation of an object, such as a heart, to compensate for this motion and/or deformation in the displayed image of the object. The motion compensation results, for example, in an image 260 as shown in FIG. 6, which is illustrated as an imaged heart having overall or gross motion compensation performed thereon. The overall or gross motion is reduced or removed to allow easier visual observation of the ROI overlay 244 with motion tracking indicators 242. Thus, the imaged heart and ROI appear more static. For example, lateral or rotational movement of the imaged heart are reduced or minimized to allow visual confirmation of motion tracking based on the motion tracking indicators. Thus, distracting motion is removed from the displayed image such that, for example, in speckle tracking applications, visual assessment of the motion tracking of the ROI to distinguish a level of tracking along the ROI (e.g., distinguish good tracking from poor tracking) is made easier.

It should be noted that based on observed motion of the motion tracking indicators 242, a user input indicating poor tracking may be received, for example, from a user to help processing by a tracking program or algorithm. For example, a user may click or drag that portion of the ROI overlay 244 at the tracking indicator 242 where there is motion, for example, using a computer mouse. The user may, for example, deform or move that portion of the ROI overlay 244 in an opposite direction and in amount about equal to the motion to indicate where and in what direction the tracking failed or wherein the tracking is poor. Thereafter, the tracking information may be updated accordingly or another tracking process performed.

Figure 7:
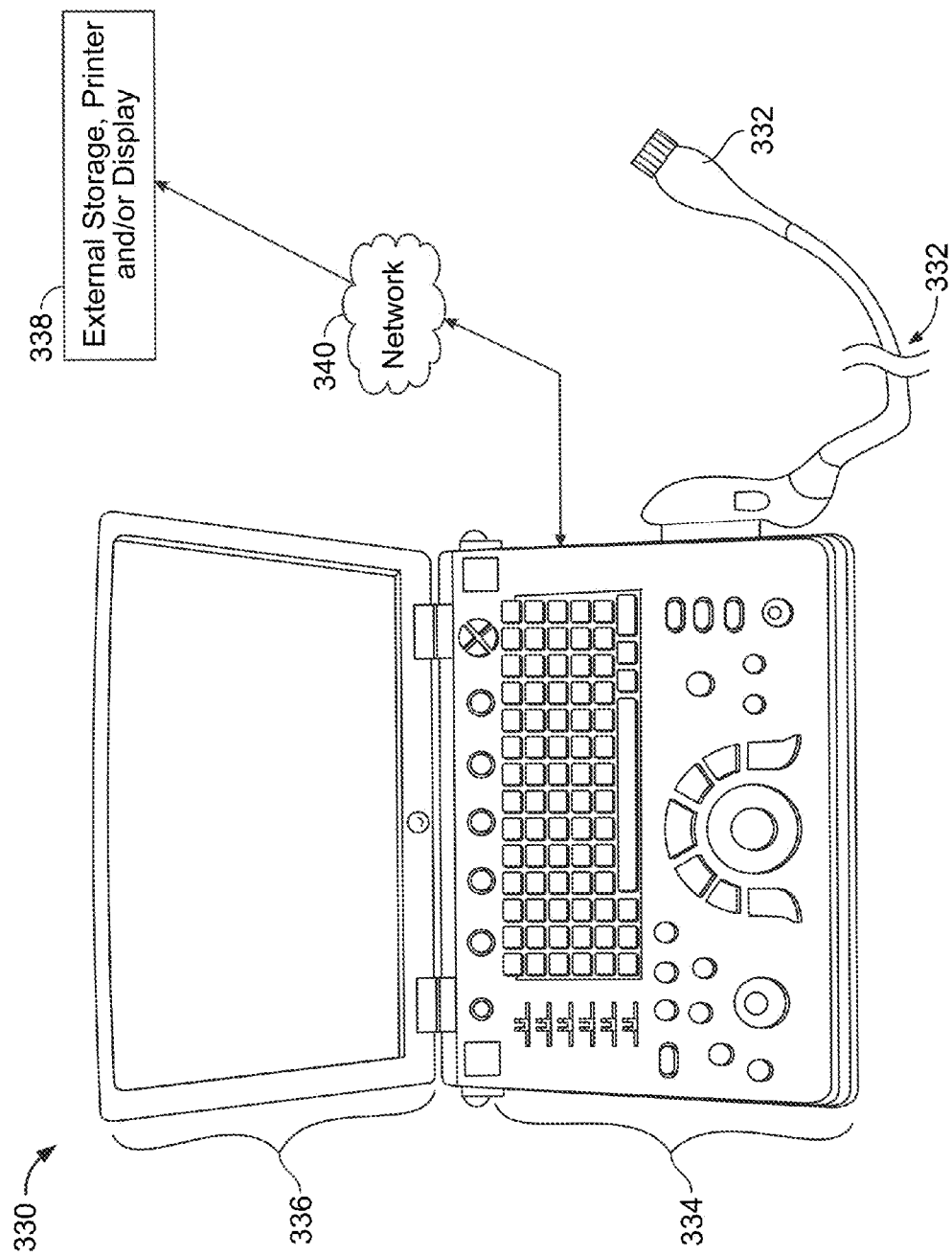
FIG. 7 is a diagram illustrating a 3D capable miniaturized ultrasound system formed in accordance with an embodiment of the invention.
Figure 8:
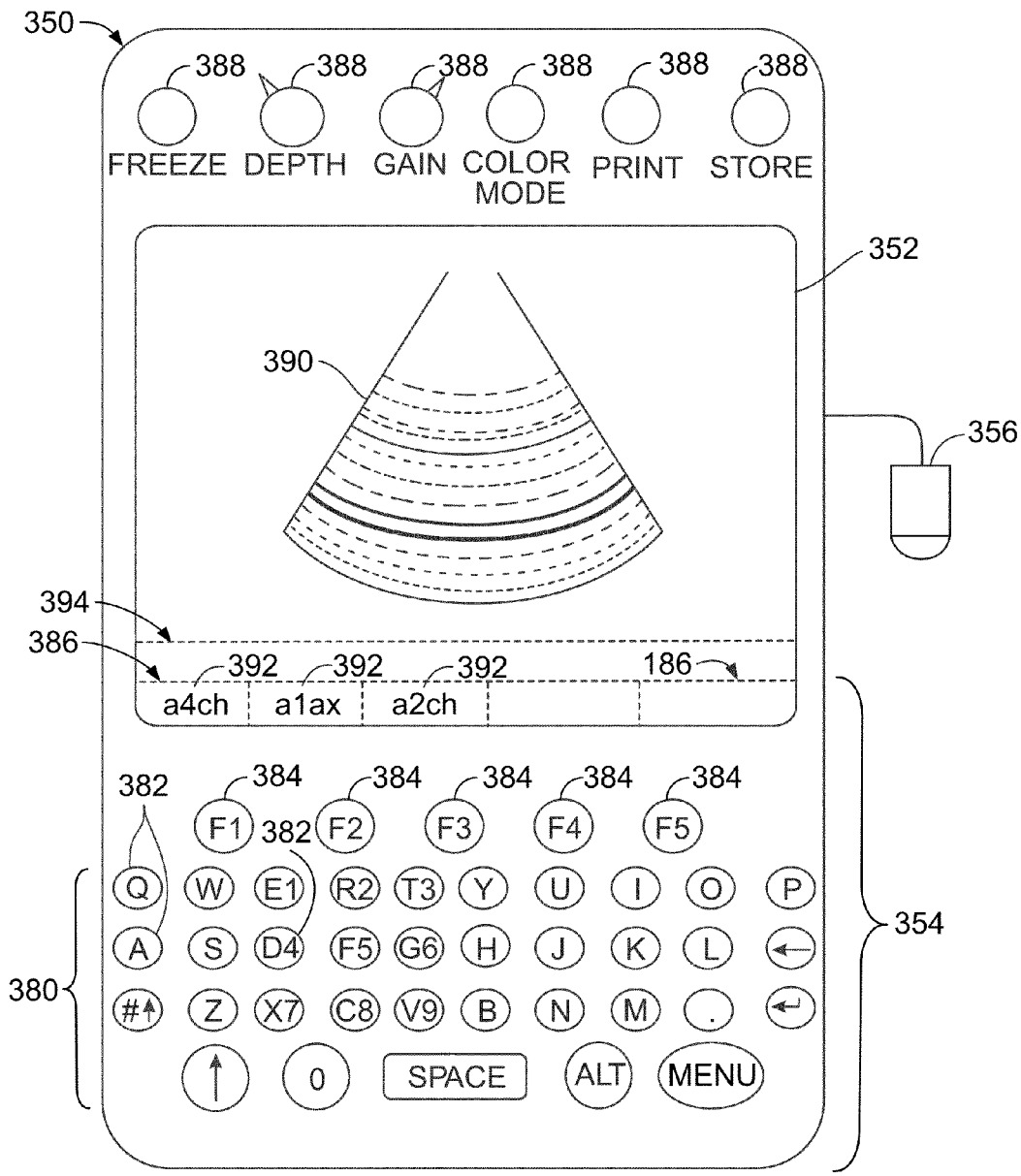
FIG. 8 is a diagram illustrating a 3D capable hand carried or pocket-sized ultrasound imaging system formed in accordance with an embodiment of the invention.
Figure 9:
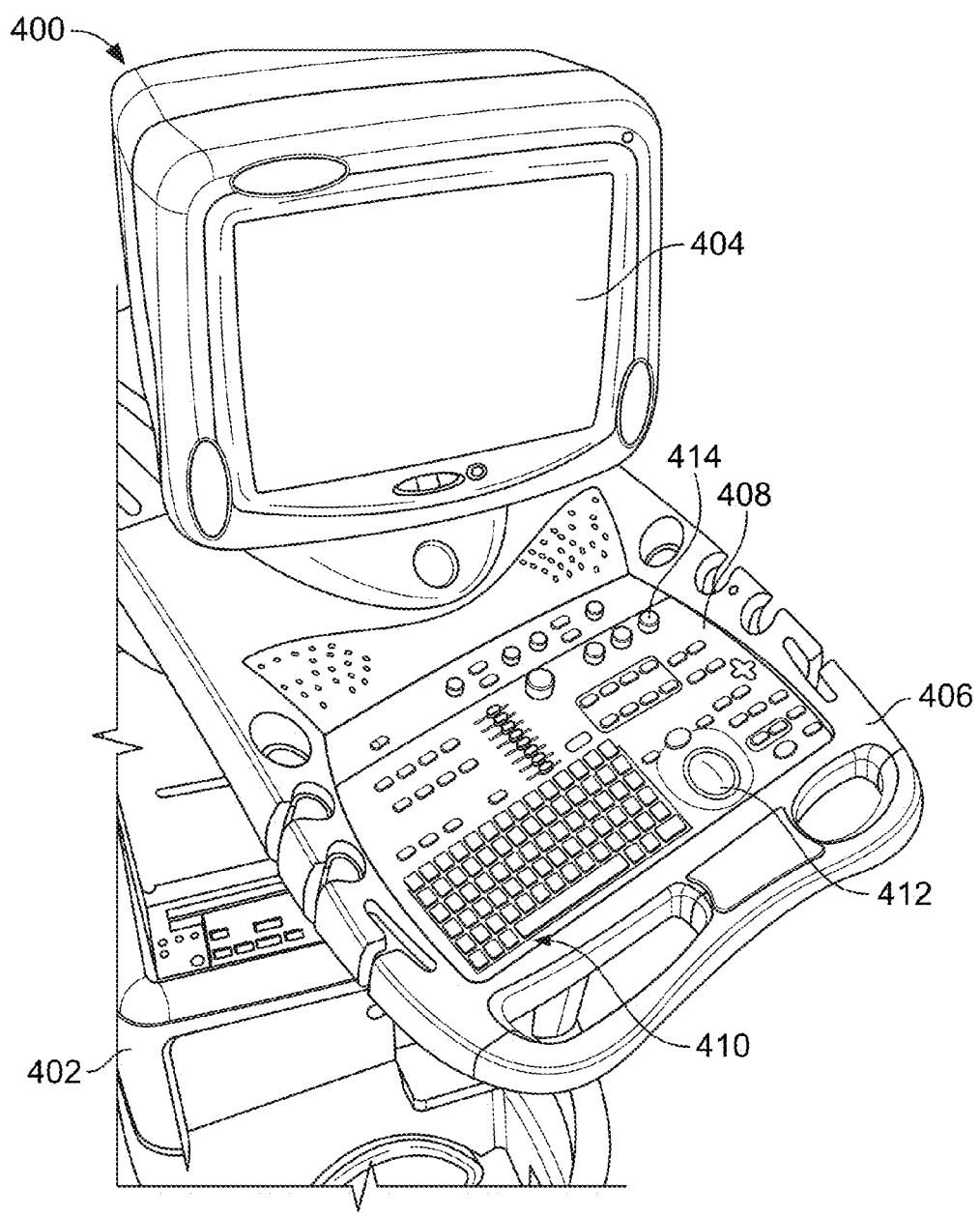
FIG. 9 is a diagram illustrating a 3D capable console type ultrasound imaging system formed in accordance with an embodiment of the present invention.

The ultrasound system 100 of FIG. 1 may be embodied in a small-sized system, such as laptop computer or pocket sized system as well as in a larger console-type system. FIGS. 7 and 8 illustrate small-sized systems, while FIG. 9 illustrates a larger system.

FIG. 7 illustrates a 3D-capable miniaturized ultrasound system 330 having a probe 332 that may be configured to acquire 3D ultrasonic data, or multi-plane ultrasonic data. For example, the probe 332 may have a 2D array of elements 104 as discussed previously with respect to the probe 106 of FIG. 1. A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display. Alternatively, the external device 338 may be a separate external display or a printer capable of receiving image data from the hand carried ultrasound system 330 and of displaying or printing images that may have greater resolution than the integrated display 336.

FIG. 8 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 190 may be displayed). A typewriter-like keyboard 380 of buttons 382 may optionally be included in the user interface 354.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. For example, the labels 392 may indicate an apical 4-chamber view (a4ch), an apical long axis view (alax) or an apical 2-chamber view (a2ch). The selection of different views also may be provided through the associated multi-function control 384. For example, the 4ch view may be selected using the multi-function control F5. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 330 may provide the same scanning and processing functionality as the system 100 (shown in FIG. 1).

FIG. 9 illustrates a portable ultrasound imaging system 400 provided on a movable base 402. The portable ultrasound imaging system 400 may also be referred to as a cart-based system. A display 404 and user interface 406 are provided and it should be understood that the display 404 may be separate or separable from the user interface 406. The user interface 406 may optionally be a touchscreen, allowing the operator to select options by touching displayed graphics, icons, and the like.

The user interface 406 also includes control buttons 408 that may be used to control the portable ultrasound imaging system 400 as desired or needed, and/or as typically provided. The user interface 406 provides multiple interface options that the user may physically manipulate to interact with ultrasound data and other data that may be displayed, as well as to input information and set and change scanning parameters and viewing angles, etc. For example, a keyboard 410, trackball 412 and/or multi-function controls 414 may be provided.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for assessing a quality of motion tracking in an imaged ultrasound object, the method comprising:
    obtaining ultrasound image data from an imaged object;
    determining motion tracking information for a region of interest of the imaged object based on the ultrasound image data;
    compensating for overall motion of the imaged object based on the determined motion tracking information;
    generating motion compensated image data using the determined motion tracking information to form an image of the object having a reduced overall motion and corresponding motion tracking indicators;
    displaying the image of the object having a reduced overall motion and the corresponding motion tracking indicators, wherein movement of the motion tracking indicators is indicative of an error in the motion tracking; and assessing a quality of the motion tracking based on movement of the motion tracking indicators along the image of the object.

2. The method in accordance with claim 1 wherein the motion tracking information comprises speckle tracking information.

3. The method in accordance with claim 1 wherein compensating for the motion further comprises compensating for gross motion of the imaged object to reduce the overall motion.

4. The method in accordance with claim 1 wherein the determining comprises determining an overall shape change of the region of interest and wherein the compensating is based on the overall shape change.

5. The method in accordance with claim 1 wherein the compensating comprises an affine transformation including at least one of scaling, rotating and translating the ultrasound image data.

6. The method in accordance with claim 1 wherein the compensating comprises a non-affine transformation based on the motion tracking information.

7. The method in accordance with claim 1 wherein the compensating comprises subtracting the motion tracking information from the ultrasound image data.

8. The method of claim 1 wherein the displaying comprises displaying the motion compensated ultrasound data with a region of interest overlay having the motion tracking indicators.

9. The method in accordance with claim 1 wherein the ultrasound image data comprises a temporal image sequence of an imaged heart.

10. The method in accordance with claim 9 wherein the determining motion tracking information comprises determining motion tracking information of a myocardium of the imaged heart.

11. The method in accordance with claim 1 further comprising receiving a user input indicating at least one of a location and an amount of a tracking failure based on the movement of the motion tracking indicators.

12. A non-transitory computer readable medium having computer readable code readable by a machine and with instructions executable by the machine to perform a method of assessing a quality of motion tracking in ultrasound image data of an object, the method comprising:
  determining motion tracking information for a region of interest of the object in the ultrasound image data;
  compensating for overall motion of the imaged object based on the determined motion tracking information;
  generating motion compensated image data using the determined motion tracking information to form an image of the object having a reduced overall motion and corresponding motion tracking indicators;
  displaying the image of the object having a reduced overall motion and the corresponding motion tracking indicators, wherein movement of the motion tracking indicators is indicative of an error in the motion tracking; and
  assessing a quality of the motion tracking based on movement of the motion tracking indicators along the image of the object.

13. The non-transitory computer readable medium in accordance with claim 12 wherein the instructions executable by the machine cause the machine to perform one of scaling, rotating and translating a displayed image of the imaged object to compensate for motion of the imaged object.

14. The non-transitory computer readable medium in accordance with claim 12 wherein the instructions executable by the machine cause the machine to display the motion compensated ultrasound data with a region of interest overlay having the motion tracking indicators.

15. A non-transitory computer readable medium in accordance with claim 12 wherein the object is a heart and wherein the region of interest is a myocardium of the heart.

16. An ultrasound imaging system, comprising:
  an ultrasound probe configured to acquire images of an object;
  a display;
  a processor having a motion compensation module configured to:
  determine motion tracking information for a region of interest of the object in the ultrasound data;
  compensate for overall motion of the imaged object based on the determined motion tracking information;
  generate motion compensated image data using the determined motion tracking information to form an image of the object having a reduced overall motion and corresponding motion tracking indicators;
  provide the display with the image of the object having a reduced overall motion and the corresponding motion tracking indicators, wherein movement of the motion tracking indicators is indicative of an error in the motion tracking; and
  assess a quality of the motion tracking based on movement of the motion tracking indicators along the image of the object.

17. The ultrasound imaging system in accordance with claim 16, wherein the motion compensation module is further configured to provide to the display the corresponding motion trackers on a region of interest overlay.

18. The ultrasound imaging system in accordance with claim 16 wherein the motion compensation module is configured to compensate for the overall motion by at least one of scaling, rotating and translating the ultrasound image data.

19. The method in accordance with claim 1 wherein the imaged object is a heart and reducing the overall motion in the image data comprises reducing one of lateral or rotational movement of a displayed image of the heart.

20. The method in accordance with claim 1 wherein the compensating comprises removing an average motion.

21. The method in accordance with claim 1 wherein the imaged object is a heart and the determining motion tracking information comprises tracking motion of a myocardium of the heart to determine the overall motion of the heart resulting from muscle motion of the heart.

22. The method in accordance with claim 21 wherein the motion tracking comprises speckle tracking and the assessing a quality of motion tracking assesses the tracking quality of the speckle tracking.

23. The method in accordance with claim 21 wherein the displaying comprising displaying a plurality of images of the heart over time having a reduced overall heart motion resulting from the compensation in combination with the motion tracking indicators.

* * * * *